Figure 1:
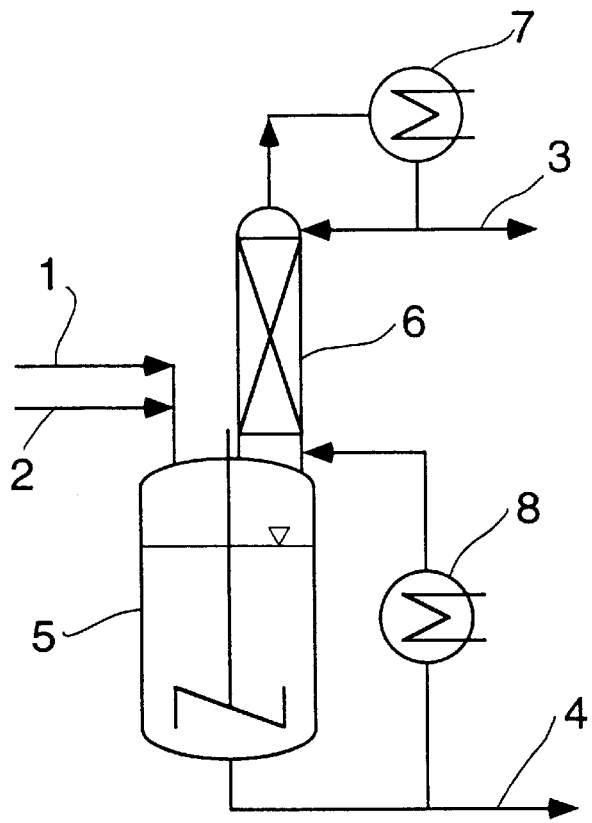

United States Patent [19]

Stroezel et al.

[11] Patent Number: 6,054,628
[45] Date of Patent: Apr. 25, 2000

[54] REACTING GRIGNARD COMPOUNDS WITH CARBONYL COMPOUNDS AND ENSUING HYDROLYSIS

[75] Inventors: Manfred Stroezel, Ilvesheim; Udo Rheude, Otterstadt; Ralf-Thomas Rahn, Mannheim; Gerd Kaibel, Lampertheim, all of Germany

[73] Assignee: BASF Aktiengesellschaft, Ludwigshafen, Germany

[21] Appl. No.: 08/955,076

[22] Filed: Oct. 21, 1997

[30] Foreign Application Priority Data

Oct. 22, 1996 [DE] Germany ............ 196 43 648

[51] Int. Cl.$^7$ ..................... C07C 35/18
[52] U.S. Cl. ............ 568/826; 568/876; 260/665 R; 260/665 G
[58] Field of Search ............ 568/876; 260/665 R, 260/665 G

[56] References Cited

U.S. PATENT DOCUMENTS

| | | |
|---|---|---|
| 4,565,894 | 1/1986 | Hertel et al. . |
| 4,754,079 | 6/1988 | Bison et al. . |
| 4,958,033 | 9/1990 | Takisawa et al. ............ 568/826 |

FOREIGN PATENT DOCUMENTS

| | | |
|---|---|---|
| 429 967 | 6/1991 | European Pat. Off. . |
| 682 005 | 11/1995 | European Pat. Off. . |
| 44 38 440 | 2/1985 | Germany . |
| 35 33 801 | 4/1987 | Germany . |
| 42 40 239 | 12/1993 | Germany . |

OTHER PUBLICATIONS

Kirk–Othmer, Ency. vol. 12, pp. 30–44.

Heuben–Weyl, Method. Org. Chem. 1973, 56–87.

*Primary Examiner*—Paul F. Shaver
*Attorney, Agent, or Firm*—Keil & Weinkauf

[57] ABSTRACT

In a process for carrying out an exothermal reaction, selected from the addition reaction of organomagnesium halide compounds to carbonyl compounds and the ensuing hydrolysis of the addition product, a considerable fraction of the heat liberated during the reaction is removed by evaporation of the solvent.

18 Claims, 3 Drawing Sheets

REACTING GRIGNARD COMPOUNDS WITH CARBONYL COMPOUNDS AND ENSUING HYDROLYSIS

The present invention relates to carrying out exothermal reactions selected from the addition reaction of Grignard compounds to carbonyl compounds and the ensuing hydrolysis of the addition product formed.

According to the prior art, Grignard reactions involving organomagnesium halides are carried out in a solvent, e.g. diethyl ether or tetrahydrofuran, cf. surveys in: Kirk-Othmer, Encyclopedia of Chemical Technology, 3rd Edition, John Wiley and Sons, 1980; and Houben-Weyl, Methoden der organischen Chemie, Metallorganische Chemie, Georg-Thieme-Verlag Stuttgart, 4th Edition, 1973. To this end, magnesium in various forms (e.g. bars, lumps, turnings) is reacted with organohalide dissolved in solvent, the Grignard reagent forming in the process and, as a rule, unreacted residual organohalide remaining in the Grignard solution formed. This way, expensive starting material is lost. Furthermore, the ensuing addition reaction of the Grignard reagent to the carbonyl compound to form the magnesium alcoholate is exothermal, so that the liberated heat of reaction has to be removed by cooling of the reaction vessel, as a rule by means of cooling water. In an ensuing hydrolysis stage the magnesium alcoholate formed is hydrolyzed. To remove the heat produced during the hydrolysis the vessel is likewise cooled. A drawback of the traditional way of carrying out the reaction in externally cooled stirred vessels is that the requisite heat removal via the wall area demands an apparatus with a large heat transfer area and therefore a large volume.

DE-A-3,328,440 discloses the use of boiling cooling by evaporation of solvent contained in the reaction mixture for the preparation of ionones. Boiling cooling is also known for the preparation of the Na salt of 2-nitropropanediol-1,3, from DE-C-3,533,801, for the liquid-phase chlorination of 1,3-butadiene, from EP-A-0,429,967, and for the preparation of terephthalic acid, from EP-A-0,682,005. What is not known is the application of boiling cooling to Grignard reactions.

It is an object of the present invention to develop an improved process for reacting Grignard compounds with carbonyl compounds and the ensuing hydrolysis, which process permits these reactions to be carried out in an apparative less complicate way.

We have found that this object is achieved if the heat produced during the exothermal addition reaction of the Grignard compounds to carbonyl compounds and the ensuing exothermal hydrolysis is removed, utilizng the simultaneous or subsequent boiling cooling, by use being made of a solvent or solvent mixture having specific boiling characteristics and this being evaporated. In so doing, the addition reaction or hydrolysis reaction is carried out at from about 0 to 10° above the boiling point of the solvent or solvent mixture.

The invention therefore relates to a process for carrying out one or more exothermal reactions selected from (a) the addition reaction of organomagnesium halide compounds of the formula RMgX, where R is $C_1$–$C_6$-alkyl, $C_2$–$C_6$-alkenyl or $C_2$–$C_6$-alkynyl or aryl and X is Cl, Br or I, to a carbonyl compound and (b) the hydrolysis of addition products of organomagnesium halide compounds of the formula RMgX, where R is C1–$C_6$-alkyl, $C_2$–$C_6$-alkenyl or $C_2$–$C_6$-alkynyl or aryl and X is Cl, Br or I, and a carbonyl compound in a solvent or solvent mixture, wherein a considerable fraction of the heat liberated during the reaction is removed by evaporation of the solvent or solvent mixture.

Preferred embodiments of the invention can be gathered from the following description and the Figures. Further preferred embodiments are defined in the subordinate claims.

FIGS. 1 to 6 show preferred embodiments for carrying out the process according to the invention.

The exothermal reactions according to the invention involve, in the first instance, the addition of organomagnesium halide compounds (Grignard compounds) of the formula RMgX, where R is $C_1$–$C_6$-alkyl, $C_2$–$C_6$-alkenyl or $C_2$–$C_6$-alkynyl or aryl, preferably ethyl, vinyl or ethynyl, and X is Cl, Br or I, preferably Cl, to a carbonyl compound, in particular a $C_{1-40}$carbonyl compound, more preferably a $C_{1-25}$compound, selected in each case from the corresponding aldehydes, ketones and esters, e.g. geranylacetone. The other possible exothermal reaction is the hydrolysis of addition products from organomagnesium halide compounds of the abovementioned formula RMgX, where the groups R and X have the abovementioned meanings, and a carbonyl compound as defined above.

Hereinafter the term reaction refers both to the addition reaction and to the hydrolysis reaction, unless stated otherwise.

According to the invention the reaction is carried out in a solvent or solvent mixture which, under the reaction conditions, boils at between 0 and 150° C., preferably at between 25 and 80° C., in particular at between 50 and 70° C., and comprises at least one ether and/or at least one amine, which may be mixed with one or more aliphatic, cycloaliphatic and/or aromatic hydrocarbons. Preferred solvents are tetrahydrofuran (THF), methyl t-butyl ether MTBE), 1,4-dioxane, diethyl ether, diphenyl ether and anisole, THF and MTBE being most strongly preferred. With the hydrolysis reaction it is usually advantageous to add a small amount of acid, preferably sulfuric acid, to the hydrolysis water. This involves, in particular, from 20 to 150 wt %, preferably from 30 to 80 wt %, of water and from 0.1 to 5 wt %, preferably from 0.5 to 3 wt %, of acid, each based on 100 wt % of solvent or solvent mixture.

The amounts preferably employed of the components used are as follows: in the addition reaction from 1 to 20 wt %, in particular from 3 to 15 wt %, of organomagnesium halide compound (Grignard reagent) and from 2 to 40 wt %, in particular from 6 to 30 wt %, of carbonyl compound; in the hydrolysis reaction from 2 to 40 wt %, in particular from 6 to 30 wt %, of addition products; the remainder in each case is solvent or solvent mixture, all the specified amounts being based on 100 wt % of reactor output with the addition reaction or hydrolysis reaction. Hereinafter the term solvent also encompasses a solvent mixture.

In a particularly preferred embodiment the solvent or solvent mixture contains an organohalide whose boiling point is lower than that of the solvent or solvent mixture and which is of the formula RX, where R and X have the abovementioned meanings. This organohalide, in particular, is residual organohalide which has not reacted during the Grignard reaction. The present process allows this organohalide to be recovered in a simple and mild way.

In one embodiment of the invention the reaction is carried out at between 0 and 150° C., preferably between 25 and 80° C., in particular between 50 and 70° C. The pressure employed with this isothermal mode of operation is preferably from 0.5 to 10 bar, in particular from 1 to 3 bar. In a particularly preferred embodiment of the invention, with this mode of operation, additional solvent is fed in during the reaction with simultaneous heating, which permits the further recovery of the abovementioned organohalide RX. It is also advantageous for highly volatile components of the reaction mixture, in particular organohalide RX, to be stripped from the reaction mixture, during the reaction, by means of vapors or (inert) gases.

If e.g. vinylmagnesium chloride is reacted with ketones in THF it proved advantageous to carry out the reaction at from 50 to 70° C., preferably at from 63 to 68° C. Under these conditions, more than 70% of the vinyl chloride present was successfully recovered from the reaction mixture. The evaporated solvent is expediently recondensed. To achieve complete depletion of the organohalide from the reaction solution, the organohalide can be stripped from the reaction output by means of inert gas or solvent vapor in a distillation column.

The isothermal mode of operation can be carried out continuously, semicontinuously or batchwise, a suitable reactor for this purpose being one with no back-mixing, with partial or even complete back-mixing, in particular a continuous or batch-type stirred vessel, loop reactor or jet tube reactor, a continuous cascade of stirred vessels or loop reactors or jet tube reactors. After the addition reaction, the reaction product is advantageously fed first to a distillation stage in which residual organo- halide is stripped from the reactor output and then to the hydrolysis stage, or is passed directly into the hydrolysis stage.

In a further refinement of the invention, the exothermal reaction is carried out continuously under adiabatic conditions. Since the adiabatic temperature increase can be considerable with the exothermal reactions and it is also possible for considerable pressures to be reached, the reaction has to take place with very short residence times to avoid the formation of unwanted by-products. In the case of the addition of vinylmagnesium chloride to ketones in THF, for example, the temperature increase may be from 30 to 100 K, depending on the reaction conditions and concentration of the solvent, so that the temperatures may rise above 100° C. and the pressures may exceed 10 bar. Suitable apparatuses include all those reactors which allow the reaction to be carried out with short residence times. Expediently use is made, for example, of reaction pumps as described e.g. in the German Patent Application P 42,20,239, mixing nozzles, static mixers, dissolvers or dynamic flow mixers with a residence time range of 1–100 s.

In the adiabatic mode of operation the reaction is carried out at from 0 to 200° C., preferably from 20 to 100° C., in particular from 30 to 80° C., at from 1 to 20 bar, preferably from 2 to 10 bar, in particular from 3 to 7 bar, and a residence time of from 0.1 to 100 s, preferably from 2 to 10 s, in particular from 3 to 8 s. After the reaction the product is depressurized, preferably in a flash zone, by means of an expansion valve, into a flash vessel. Expediently the vapors produced during flashing are then condensed. Since the adiabatic mode of operation may give rise to very high temperatures, the starting materials to be reacted are advantageously cooled prior to the reaction. In a preferred embodiment, highly volatile components, in particular organohalide RX, are stripped from the reactor output, after the reaction, by means of vapors or (inert) gases or, in analogy to the isothermal mode of operation, additional solvent is supplied with simultaneous heating. Again, therefore, unreacted organohalide can be separated off in a distillation column by the reaction solution being stripped with gaseous or vaporous stripping media.

Said stripping of highly volatile components is preferably carried out in a distillation column. Generally suitable as distillation columns for this purpose and for purifying the reaction product of the addition reaction or hydrolysis reaction are columns comprising solids-insensitive internals, e.g. dual-flow plates, bubble-cap plates or valve plates, or special solids-insensitive arranged packings made of sheet metal, glass or porcelain, or packing elements.

The novel process allows the reaction to be carried out in apparatuses of small volume and at the same time permits a recovery of organohalide RX whose boiling point is lower than that of the solvent. This recovery of the highly volatile organohalide may, if it was not completed during the addition reaction, be effected in the hydrolysis stage. This is less preferable, however, since the distillate fraction comprising the organohalide contains not only solvents, but also water which has to be removed by means of a further process step before the distillate fraction is advantageously recycled into the preparation stage of the Grignard compound.

A further advantage of the novel process in comparison with processes involving conventional external cooling of the stirred vessel is that accretions of solids on the heat exchanger can be avoided. This means that the previously used systems involving external cooling are no longer required.

FIG. 1 shows a reaction apparatus, suitable for carrying out the reaction isothermally, comprising a stirred vessel (5) with a fitted column (6), condenser (7) and evaporator (8). Via the lines (1) and (2) the starting materials, i.e. either the organomagnesium halide compound (Grignard reagent), a carbonyl compound and solvent/solvent mixture or the addition compound, water and solvent/solvent mixture, with or without acid, are introduced into the stirred vessel (5) and reacted there. The reaction product is drawn off via the line (4), while the evaporated solvent/solvent mixture, which may or may not be mixed with organohalide, is distilled and then drawn off via line (3). A suitable reactor (5) is a stirred vessel or a loop reactor, with or without a mixing nozzle.

Figure 2:
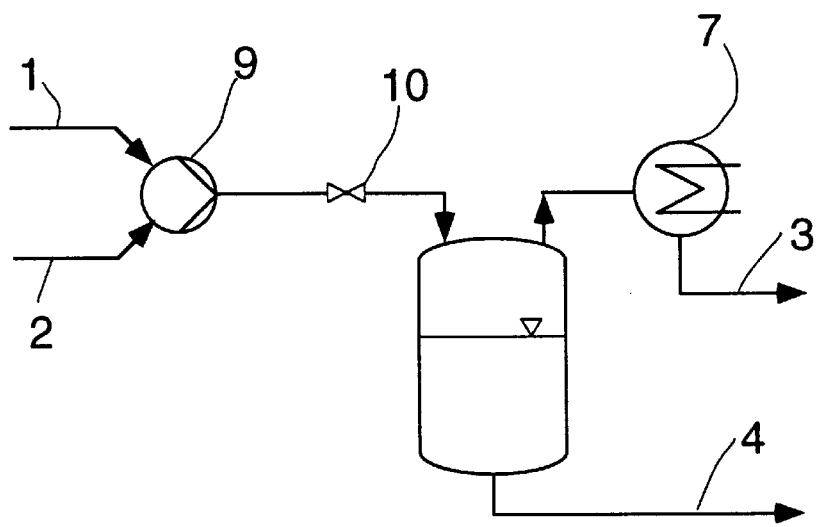
Figure 3:
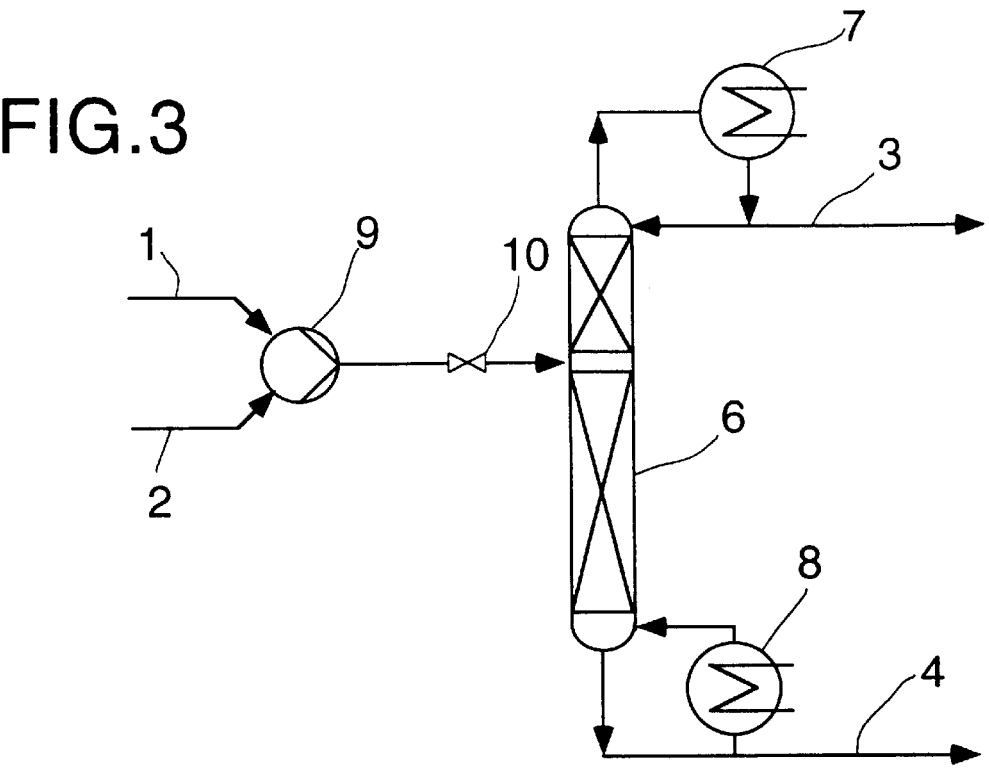

FIG. 2 shows a reaction pump (9) into which the starting materials are fed via lines (1) and (2) and in which they are reacted.

The reaction product is then flashed via the expansion valve (10) and passed into a vessel in which a separation into liquid and vaporous substances takes place. Identical reference numerals in FIG. 2 have the same meanings as in FIG. 1. In the adiabatic mode of operation shown in FIG. 2, unreacted organohalide can be separated off by stripping with gaseous or vaporous stripping media, either in the vessel or in a distillation column (not shown) downstream of the expansion valve.

In the following FIGS. 3 to 6 identical reference numerals have the same meanings as in FIGS. 1 and 2.

Figure 4:
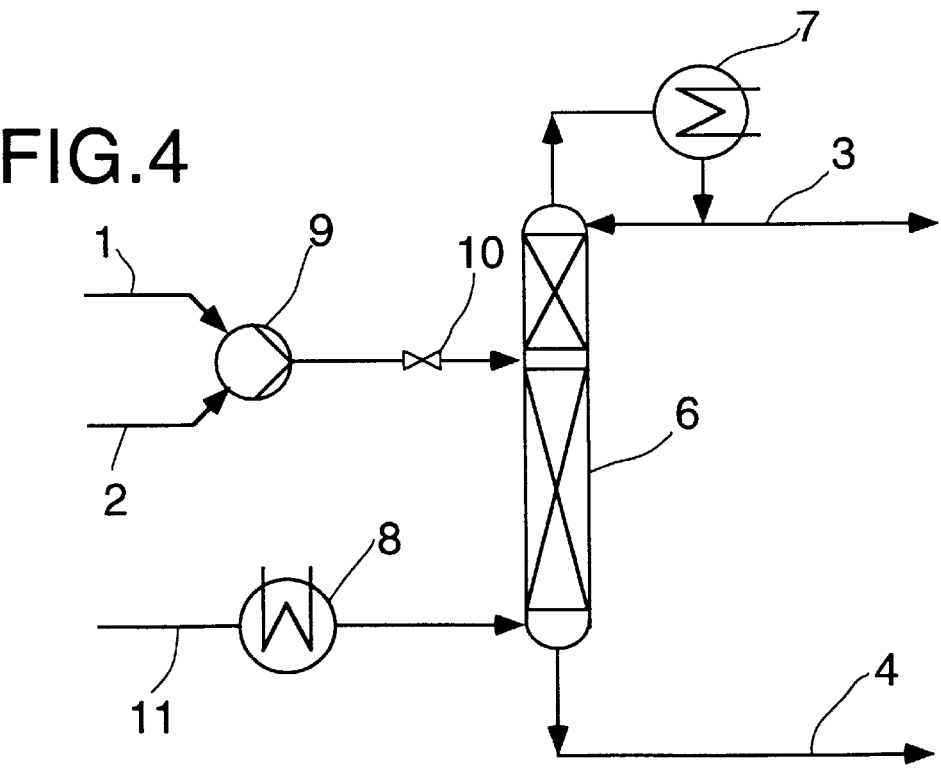
Figure 5:
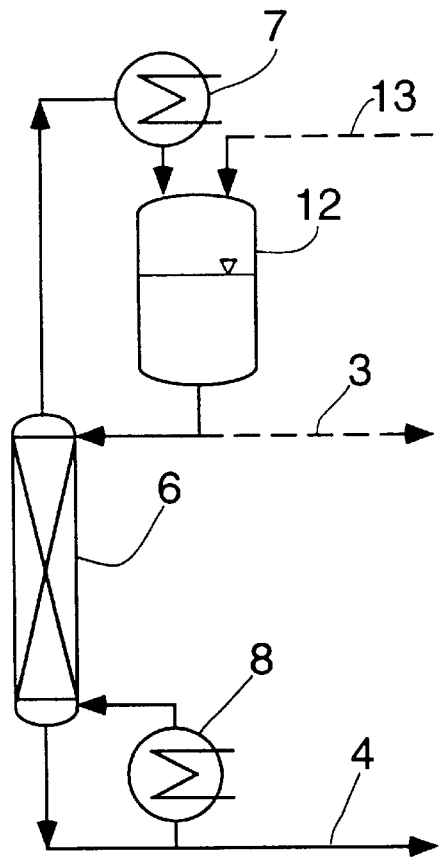
Figure 6:
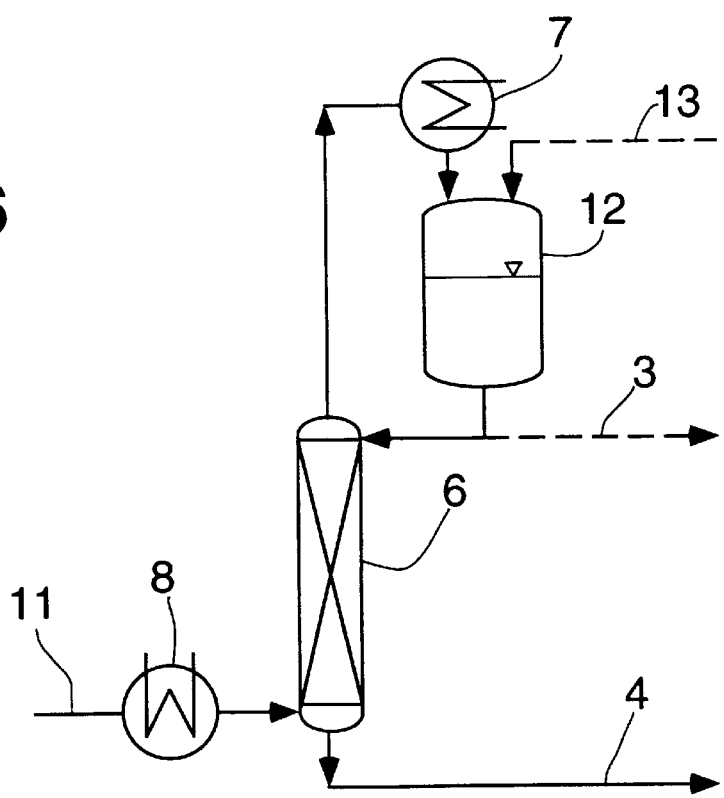

FIG. 3 again shows the adiabatic mode of operation, the reactor output after flashing being fed into the distillation column (6) so that essentially organohalide-free product can be drawn off from the column bottom via line (4). It is thus possible to attain organohalide levels in the bottom product which are in the ppm range. To prevent the bottom product from becoming unduly concentrated, which may lead to precipitation of the magnesium alcoholate, it is expedient to feed additional solvent (11) into the column bottom, as shown in FIG. 4. In addition to an upward mode of operation in which the reaction product is passed into a still on which the low-boiling components are distilled off, the downward mode of operation shown in FIG. 5 proves advantageous, in which the reactor output (13) is fed, via the stock tank (12), to the head of a batch-type distillation column (6). In this case the organohalide-rich distillate (3) is drawn off at the head and returned into the stock tank (12) where mixing takes place with further reactor output (13). The virtually organohalide-free bottom product (4) is drawn off. Again it may be advantageous to feed fresh solvent (11) into the column bottom, with simultaneous heating, as shown in FIG. 6, to allow other organohalide to be recovered.

The invention is explained in more detail with reference to the following Examples which represent preferred embodiments of the invention.

EXAMPLES

Example 1 (Addition reaction)

3500 g of a solution at 50° C. which contains 4.6 wt % of vinyl chloride, 89.0 wt % of THF and 6.4 wt % of vinylmagnesium chloride are reacted continuously, over a period of 1 h, with 497 g of geranylacetone (molar mass: 194) (inlet temperature 50° C.) in a stirred vessel at 65° C. This produces a distillate of 815 g having a composition of 15 wt % of vinyl chloride and 85 wt % of THF and a liquid reactor output of 3182 g having a composition of 76.1 wt % of THF, 1.2 wt % of vinyl chloride and 22.6 wt % of the addition product chloromagnesium-nerolidolate (molar mass: 281). 76% of the vinyl chloride contained in the feed stream is re-covered in the distillate. External cooling of the stirred vessel with cooling water is unnecessary.

Example 2 (Addition reaction)

As in Example 1, 3500 g of a solution at 50° C. which contains 4.6 wt % of vinyl chloride, 89.0 wt % of THF and 6.4 wt % of vinylmagnesium chloride, are reacted continuously, over a period of 1 h, with 497 g of geranylacetone (molar mass: 194) (inlet temperature 50° C.) in a stirred vessel at 65° C. Additionally, 1000 g of liquid THF are pumped into the reaction vessel, and the vessel is heated in such a way, with a heat output of about 140 W, that the same amount of bottom output is obtained as if no additional THF had been supplied. This produces a distillate of 1815 g having a composition of 7.7 wt % of vinyl chloride and 92.3 wt % of THF and a liquid reactor output of 3182 g having a composition of 76.1 wt % of THF, 1.2 wt % of vinyl chloride and 22.6 wt % of the addition product chloromagnesium nerolidolate (molar mass: 281). 87% of the vinyl chloride contained in the feed stream is recovered in the distillate.

Example 3 (Stripping of the reactor output of an addition reaction)

The head of a column comprising an arranged packing with a length of 1.10 m and a diameter of 50 mm is charged with 757 g/h of a mixture of 3.5 wt % of vinyl chloride, 66 wt % of THF, 28.2 wt % of the addition product chloromagnesium nerolidolate (molar mass: 281) and 1.7wt % of further high-boiling components. The column bottom is supplied with 594 g/h of pure THF as a vapor. At a reflux ratio of 2, a distillate of 552 g/h, consisting of 95.2 wt % of THF and 4.8 wt % of vinyl chloride and a liquid bottom product of 799 g/h having a composition of 71.1 wt % of THF, 27.3 wt % of addition product, 100 ppm of vinyl chloride and 1.6 wt % of high-boiling components is obtained. >99% of the vinyl chloride contained in the feed is recovered in the distillate.

Example 4 (Hydrolysis reaction)

3792 g of a solution at 60° C. which contains 79.1 wt % of THF, 2.8 wt % of vinylmagnesium chloride, 17.4 wt % of addition product chloromagnesium nerolidolate (molar mass: 281) and 0.9 wt % vinyl chloride are admixed, in a stirred vessel, over a period of 1 h, with 1814 g of about 2 wt % strength sulfuric acid at 36° C., and the addition product is hydrolyzed. The hydrolysis produces a distillate of about 130 g/h at 55° C., which contains 64 wt % of THF, 5 wt % of water 13 wt % of ethylene. and 18 wt % vinyl chloride. External cooling of the stirred vessel with cooling water is unnecessary. In the destillate 70% of the vinyl chloride are separated and can be supplied to a further processing step.

We claim:

1. A process for carrying out a Grignard reaction comprising the exothermal reaction steps of
   a) reacting an organohalide RX, where R is $C_1$–$C_6$-alkyl, $C_2$–$C_6$-al-kenyl or $C_2$–$C_6$-alkynyl or aryl and X is Cl, Br or I, with magnesium to give an organomagnesium halide compounds of the formula RmgX,
   b) reacting the organomagnesium halide compound of the formula RMgX with a carbonyl compound to give an addition product, and
   c) hydrolyzing the addition product of the organomagnesium halide compound of the formula RMgX and the carbonyl compound, in a solvent or a solvent mixture, which process is characterized in that either the exothermal reaction step b) or the exothermal reaction step c) or both steps b) and c) are carried out in the absence of external cooling, and wherein a considerable fraction of the heat liberated during the exothermal reaction which is carried out in the absence of external cooling is removed by evaporation of the solvent or solvent mixture.

2. The process of claim 1, wherein the organohalide RX is the solvent or constitutes a part of the solvent mixture and where RX has a boiling point which is lower than that of other constituents of the solvent mixture.

3. The process of claim 1, wherein the solvent or solvent mixture under the reaction conditions has a boiling point of between 0 and 150° C. and contains at least one ether or at least one amine or a mixture thereof, and may further comprise one or more aliphatic, cycloaliphatic or aromatic hydrocarbons.

4. The process of claim 1, wherein the reaction step which is carried out in the absence of external cooling is carried out at between 0 and 150° C.

5. The process 1, wherein the reaction step which is carried out in the absence of external cooling is carried out at from 0.5 to 10 bar.

6. The process of claim 4, wherein highly volatile components of the reaction mixture are stripped from the reaction mixture of the reaction step which is carried out in the absence of external cooling, during the reaction by means of vapor or gases.

7. The process of claim 1, wherein the reaction step which is carried out in the absence of external cooling is carried out continuously at from 0 to 200° C., at from 1 to 20 bar and a residence time of from 0.1 to 100 s, and after the reaction the product is depressurized.

8. The process of claim 7, wherein the vapor produced in the course of depressurizing is condensed.

9. The process of claim 7, wherein highly volatile components of the reaction mixture are stripped from the reactor output, after the reaction by means of vapor or gases.

10. The process of claim 6, characterized in that said stripping is carried out in a distillation column.

11. The process of claim 3, wherein the solvent or solvent mixture under the reaction conditions has a boiling point of between 25 and 80° C.

12. The process of claim 1, wherein the reaction step which is carried out in the absence of external cooling is carried out at between 25 and 80° C.

13. The process of claim 1, wherein the reaction step which is carried out in the absence of external cooling is carried out at from 1 to 3 bar.

14. The process of claim 6, wherein the highly volatile component of the reaction mixture is the organohalide RX.

15. The process of claim 7, wherein the reaction step which is carried out in the absence of external cooling is carried out continuously at from from 20 to 100° C.

16. The process of claim 7, wherein the reaction step which is carried out in the absence of external cooling is carried out continuously at from 2 to 10 bar.

17. The process of claim 7, wherein the reaction step which is carried out in the absence of external cooling is carried out continuously at a residence time of from 2 to 10 s.

18. The process of claim 1, wherein the exothermal reaction step b) is carried out in the absence of external cooling.

* * * * *

UNITED STATES PATENT AND TRADEMARK OFFICE
CERTIFICATE OF CORRECTION

PATENT : 6,054,628
DATED : April 25, 2000
INVENTOR(S) : STROEZEL et al.

It is certified that error appears in the above-identified patent and that said Letters Patent is hereby corrected as shown below:

Column 6, claim 1, line 14, change "$R_{mg}X$" to --$RM_gX$--

Signed and Sealed this

Twentieth Day of March, 2001

Attest:

NICHOLAS P. GODICI

*Attesting Officer*       *Acting Director of the United States Patent and Trademark Office*